(12) United States Patent
Chou et al.

(10) Patent No.: US 9,993,416 B1
(45) Date of Patent: Jun. 12, 2018

(54) HYDRATING ELASTOMERIC FLEXIBLE ARTICLE WITH NATURAL BIOACTIVES AND MANUFACTURING METHOD

(71) Applicant: SHEN WEI (USA) INC., Union City, CA (US)

(72) Inventors: Belle L. Chou, Union City, CA (US); Sisitha Sudarshana, Homagama (LK); Athawuda Arachchige Ranthi Manahari Dias, Athurugiriya (LK)

(73) Assignee: SHEN WEI (USA) INC., Union City, CA (US)

( * ) Notice: Subject to any disclaimer, the term of this patent is extended or adjusted under 35 U.S.C. 154(b) by 0 days. days.

(21) Appl. No.: 15/495,875

(22) Filed: Apr. 24, 2017

(51) Int. Cl.

| | |
|---|---|
| *A61K 36/79* | (2006.01) |
| *A61K 36/076* | (2006.01) |
| *A61K 36/185* | (2006.01) |
| *A61K 8/73* | (2006.01) |
| *A61K 8/02* | (2006.01) |
| *A61Q 19/00* | (2006.01) |
| *A61K 8/97* | (2017.01) |
| *C12P 19/04* | (2006.01) |
| *C12P 19/14* | (2006.01) |

(52) U.S. Cl.
CPC .............. *A61K 8/73* (2013.01); *A61K 8/0204* (2013.01); *A61K 8/97* (2013.01); *A61Q 19/007* (2013.01); *C12P 19/04* (2013.01); *C12P 19/14* (2013.01); *C12Y 302/01025* (2013.01); *A61K 2800/594* (2013.01); *A61K 2800/84* (2013.01); *A61K 2800/85* (2013.01)

(58) Field of Classification Search
None
See application file for complete search history.

(56) References Cited

U.S. PATENT DOCUMENTS

| | | |
|---|---|---|
| 6,274,154 B1 | 8/2001 | Chou |
| 6,953,582 B2 | 10/2005 | Chou |

FOREIGN PATENT DOCUMENTS

WO  WO 03057893 A1 * 7/2003 ............ A61K 31/70

OTHER PUBLICATIONS

A. V. Rawlings & C.R. Harding, "Moisturization and Skin Barrier Function", Dermatologic Therapy, vol. 17, pp. 43-48, 2004.
Rawlings and Matts, "Stratum Corneum Moisturization at the Molecular Level: an Update in Relation to the Dry Skin Cycle", the Journal of Investigative Dermatology, 124, pp. 1099-1110, 2005.
Seung Hun Lee, et.al, "An Update of the Defensive Barrier Function of Skin", Yonsei Medical Journal, vol. 47, No. 3, pp. 293-306, 2006.
Sylvie Verdier-Sévrain & Frédéric Bonté, "Skin Hydration: a Review on its Molecular Mechanisms", Journal of Cosmetic Dermatology, 6, pp. 75-82, 2006.
Josias H. Hamman, "Composition and Applications of Aloe vera Leaf Gel", Molecules, 13, pp. 1599-1616, 2008; DOI: 10.3390/molecules13081599.
F. Bonté, "Skin Moisturization Mechanisms: New Data", Annales Pharmaceutiques Francaises, 69, pp. 135-141, 2011.
Joseph Fowler, "Understanding the Role of Natural Moisturizing Factor in Skin Hydration", Practical Dermatology, pp. 36-40, Jul. 2012.
Tewolde Mulu et.al, "Medicated Evaluation of Aloe Vera: Overview on Characteristics and Application", World Journal of Nutrition and Health, vol. 3, No. 1, pp. 1-7, 2015; doi: 10.12691/jnh-3-1-1.

* cited by examiner

*Primary Examiner* — Kyle Purdy
(74) *Attorney, Agent, or Firm* — Intellectual Property Law Group LLP (57) ABSTRACT

Disclosed are a mixture of modified polysaccharides and the process of making the modified polysaccharides. Embodiments disclose processing and applying a preparation of the mixture of modified polysaccharides in combination with other bioactive ingredients in aloe, such as amino acids onto the inside surface of a polymer elastomeric flexible article, for example a glove, to enhance the water holding capacity and to regulate pH of the user's skin through effective epidermal penetration.

23 Claims, 5 Drawing Sheets

HYDRATING ELASTOMERIC FLEXIBLE ARTICLE WITH NATURAL BIOACTIVES AND MANUFACTURING METHOD

BACKGROUND OF THE INVENTION

1. Field of the Invention

The exemplary embodiment(s) of the present invention generally relates to a single use polymer elastomeric flexible article for application to a user's skin. More specifically, the exemplary embodiment(s) of the present invention relates to methods of modifying and applying a coating containing specific molecular size aloe polysaccharides which affect specific biological mechanisms.

2. Background

A principal problem is that hands become dry and cracked after frequent cleansing and washing. This is due to the removal of the skin's natural moisturizing factors (NMF) and lipid barrier. Repeated use of cleansing agents such as soaps, sanitizers and liquid hand wash exacerbate the problem because it causes the skin's pH to increase where an acidic pH is a key factor in maintaining healthy skin. A range between pH 5-5.5 is ideal for the skin to perform its role as a barrier by retarding the entry of pathogenic microorganisms and preventing the occurrence of skin disease.

A solution to this problem has been aloe coated gloves that claim skin moisturizing and therapeutic properties; however, the aloe is not absorbed into the skin because it has a higher molecular weight, such as above 2000 kDa. The bulky native polysaccharide configuration makes aloe from the coating almost impossible to absorb into the skin, which is a critical factor for long term skin benefits.

Accordingly, there is a need to reduce the molecular weight of native polysaccharides found in aloe to allow greater absorption into the skin. With increased absorption of modified aloe polysaccharides, water retention is enhanced in the user's skin thereby increasing the moisture content. Furthermore, there is also a need to maintain the skin's range between pH 5-5.5.

SUMMARY

According to an embodiment of the present invention, there is skin hydrating elastomeric flexible article, such as a fluid impermeable polymer disposable glove, comprising an outside surface and an inside surface. The inside surface configured to contact the skin of the wearer. There is a coating applied to the inside surface comprising modified aloe polysaccharides, having a molecular size ranging from less than 1 kDa-200 kDa in combination with other aloe active ingredients such as naturally occurring amino acids. The coating is dry and comprises the modified aloe polysaccharides in three fractions, and the coating is dissolvable to release the three fractions of modified polysaccharides. Each fraction targets a different site in the stratum corneum.

According to an embodiment of the present invention, there is a processing method of making modified aloe polysaccharides. The method comprises preparing a mixture of a powdered polysaccharide content with a liquid medium; filtering a first fraction of a first range of molecular sized polysaccharides from the mixture; reacting the mixture with an enzyme and generating a reacted product; filtering a second fraction of a second range of molecular sized polysaccharides from the reacted product; and filtering a third fraction of a third range of molecular sized polysaccharides from the reacted product.

According to an embodiment of the present invention, there is a processing method that can concentrate and isolate at least sixteen naturally occurring amino acids present in the aloe extract.

In further embodiments of the present invention, the method comprises freeze drying each of the filtered first fraction, filtered second fraction and filtered third fraction. The method further comprises combining an effective amount of the freeze dried first, second and third fractions. According to another embodiment, before freeze drying the filtered second fraction, the filtered second fraction is encapsulated with liposomes.

According to an embodiment of the present invention, there is a coating comprising at least modified aloe polysaccharides having molecular weight sizes of 100-200 kDa, 1-5 kDa, and less than 1 kDa.

According to an embodiment of the present invention, there is an article, such as a glove, having a preparation that enhances the ability of the user's skin to retain water and thereby increase the moisture content by 2-5%.

According to an embodiment of the present invention, the preparation has concentrated amino acids that help the skin to maintain its pH between a pH 5-5.5.

According to a further embodiment of the present invention, there is a method of making an elastomeric flexible article having a preparation of modified polysaccharides made according to a process of the present invention. The method includes applying a mixture of the modified polysaccharides and a liquid medium to a skin-contacting inner surface of the article and dehydrating the preparation onto the inner surface of the article.

These features, advantages and other embodiments of the present invention are further made apparent, in the remainder of the present document, to those of ordinary skill in the art.

BRIEF DESCRIPTION OF THE DRAWINGS

In order to more fully describe embodiments of the present invention, reference is made to the accompanying drawings. These drawings are not to be considered limitations in the scope of the invention, but are merely illustrative.

DETAILED DESCRIPTION OF SPECIFIC EMBODIMENTS

The description above and below and the drawings of the present document focus on one or more currently preferred embodiments of the present invention and also describe some exemplary optional features and/or alternative embodiments of the present invention. The description and drawings are for the purpose of illustration and not limitation. Those of ordinary skill in the art would recognize variations, modifications, and alternatives. Such variations, modifications, and alternatives are also within the scope of the present invention. Section titles are terse and are for convenience only.

Throughout the description and drawings, example embodiments of the present invention are given with reference to specific configurations. It will be appreciated by those of ordinary skill in the art that the present invention can be embodied in other specific forms. Those of ordinary skill in the art would be able to practice such other embodiments of the present invention without undue experimentation. The scope of the present invention, for the purpose of the present patent document, is not limited merely to the specific example embodiments of the present invention or alternatives of the foregoing description.

Various embodiments of the present invention illustrated in the drawings may not be drawn to scale. Rather, the dimensions of the various features may be expanded or reduced for clarity. In addition, some of the drawings may be simplified for clarity. Thus, the drawings may not depict all of the components of a given apparatus (e.g., device) or method. Unless the meaning is clearly to the contrary, all ranges set forth herein are deemed to be inclusive of the endpoints.

Figure 3:
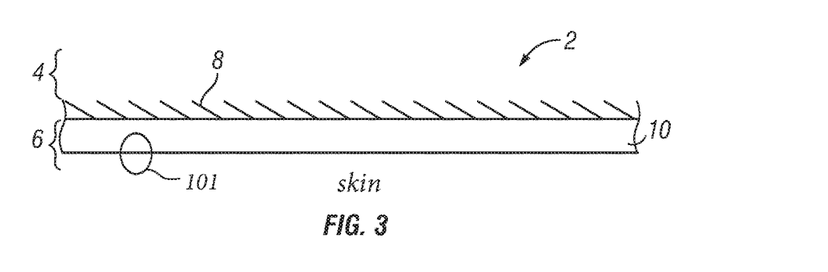
FIG. 3 illustrates a cross sectional view of a polymer elastomeric flexible article comprising a coating on the inside surface of the article, the coating comprising modified aloe polysaccharides in combination with naturally occurring amino acids, according to an embodiment of the present invention.

According to an embodiment of the present invention, there is an elastomeric flexible article, such as a fluid impermeable disposable glove 2 comprising a layer 8 having an outside surface 4 and an inside surface 6. The outside surface 4 faces the external environment and the inside surface 6 faces the user's skin. A coating 10 is applied to the inside surface 6. The coating 10 is modified aloe polysaccharides, having a molecular size ranging from less than 1 kDa-200 kDa in combination with other aloe active ingredients such as amino acids. These amino acids are a collection of naturally occurring amino acids in aloe, which include but are not limited to, a total of sixteen amino acids. The sixteen amino acids reduce the pH of the skin and help the skin maintain its natural skin pH, at an optimum level. The amino acids are activated by the warm and moist environment on the skin when the coating substantially touches the user's skin. Using a processing method as detailed in this present invention, the concentration of the naturally occurring amino acids is significantly increased. The coating 10 enhances the retention of water in the user's skin and additionally reduces the skin's pH due to the acidic nature of the aloe amino acids.

An embodiment of the present invention is an elastomeric flexible article having a layer 8. The layer 8 comprises an inside surface 6 and an outside surface 4. A coating 10 is applied to the inside surface 6 and comprises a mixture of modified natural polysaccharides (MP) and bioactive materials. In an embodiment, the bioactive materials may comprise at least sixteen naturally occurring amino acids found in aloe. The modified natural polysaccharides and other bioactive materials of the coating 10 are selected from the species aloe vera, and subjected to an enzymatic processing sequence in order to isolate modified aloe polysaccharide fragments with specific molecular sizes. The process begins with larger aloe polysaccharides which are modified into three sets of lower molecular sizes. These lower molecular weight fractions have a content of concentrated amino acids from aloe and are combined in a specific weight percentage formulation.

Figure 1A:
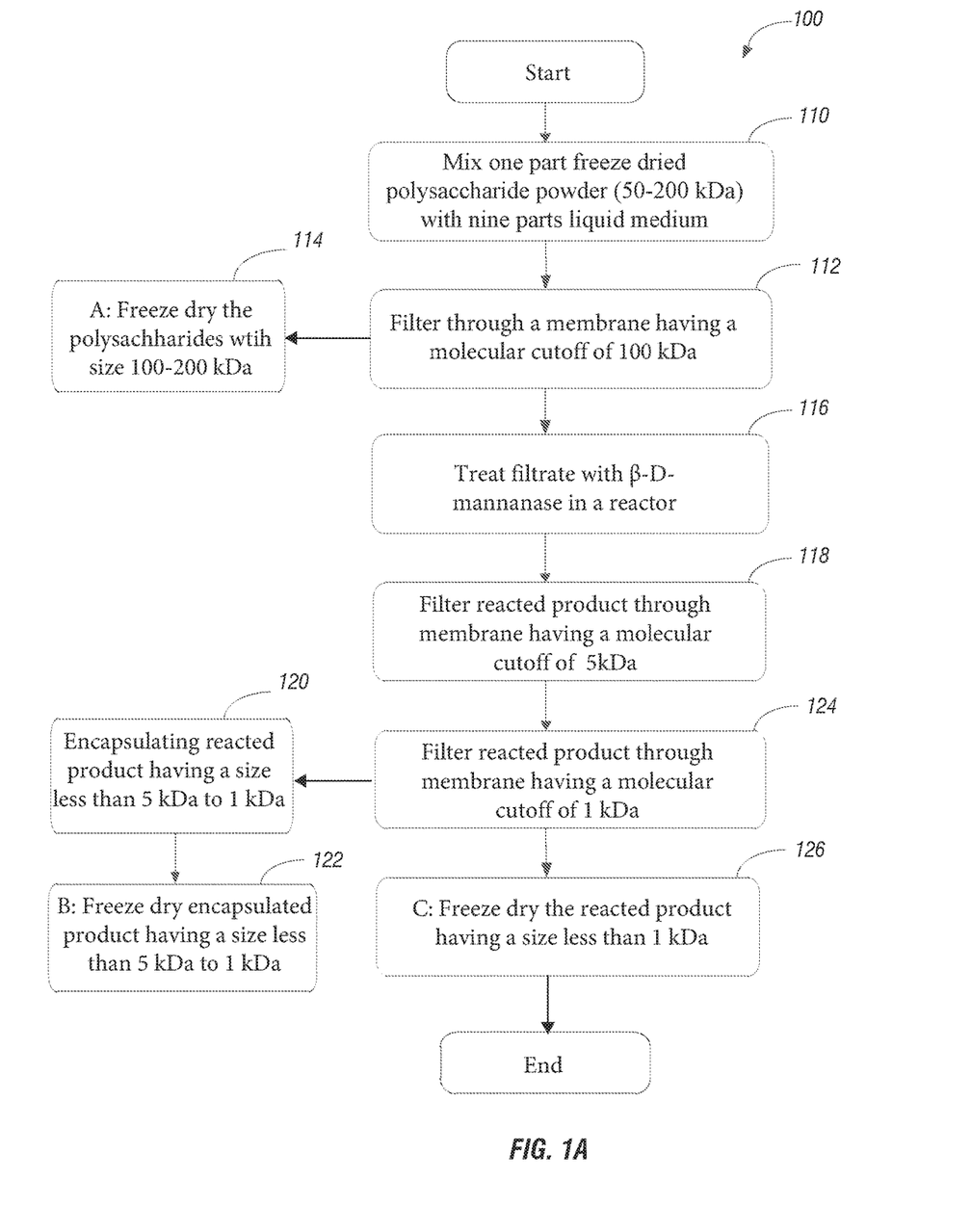
FIG. 1A illustrates a process for modification of aloe polysaccharides, according to an embodiment of the present invention.

Specific modified aloe polysaccharide methods of the present invention are summarized below. One method 100 of making modified natural aloe polysaccharide fraction is illustrated in FIG. 1A. One formulation of a modified aloe polysaccharide comprises a mixture preferably with a molecular weight ratio of 10:30:60 of 100-200 kDa, 1-5 kDa, and less than 1 kDa, respectively. Immuno 10® (from ALOECORP, INC), is a freeze dried aloe powder, with a concentrated polysaccharide content of molecular weight of 50-200 kDa. To isolate natural polysaccharide with a molecular weight between 100-200 kDa, one part of the freeze dried aloe powder is mixed with nine parts of the liquid medium, preferably water (step 110) and filtered through a membrane having a molecular size cut-off 100 kDa (UF Membrane-LY from Synder Filtration Inc.) 112. The isolated natural polysaccharide with a molecular weight between 100-200 kDa is then freeze dried 114, fraction A. The enzymatic hydrolysis occurs when the filtrate is treated with an enzyme, preferably β-D-mannanase (PROZOMIX LTD, UK.) in a closed reaction vessel to cleave the aloe polysaccharides into medium polysaccharide units 116. The β-D-mannanase dose is 2 g per 100 g of the polysaccharide. To isolate natural polysaccharide having molecular weight between 1-5 kDa, the above β-D-mannanase treated fraction is filtered through a membrane having a molecular size cut-off 5 kDa (UF Membrane-MT from Synder Filtration Inc.) 118. However, other enzymes such as cellulase can be contemplated. The isolated natural polysaccharide molecular weight between 1-5 kDa, is encapsulated with liposomes 120 and freeze dried 122, fraction B. To isolate polysaccharide molecular weight less than 1 kDa, the filtrate is filtered through a membrane having a molecular size cut-off of 1 kDa (UF Membrane-XT from Synder Filtration Inc.) 124. The isolated natural polysaccharide with a molecular weight less than 1 kDa, is freeze dried 126, fraction C. A yield of a high concentration of at least sixteen naturally occurring amino acids present in aloe is also obtained from the final filtration.

TABLE 1

Amino acid content before and after processing

| | Amino acid content |
|---|---|
| Aloe - before processing | ~15 mol/mg |
| Aloe - after processing | ~150 mol/mg |

In the process 100, the pH of the reaction medium is 6-7 pH and the temperature of the reactor is maintained at approximately 50-60° C., while controlling the time, to obtain the desired yield percentages.

Figure 2:
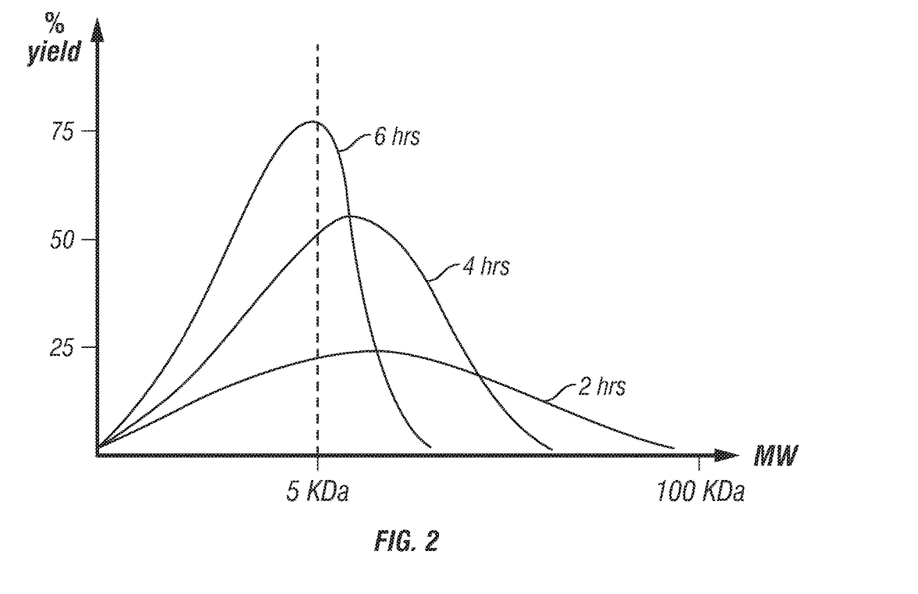
FIG. 2 illustrates time dependency over the yield percentage with desired molecular size of modified aloe polysaccharide, according to an embodiment of the present invention.

The time dependency over the yield percentage with desired molecular size of modified aloe polysaccharide is shown in FIG. 2. The reaction time is important to obtain the desired amount of aloe fragments. It is preferable to control the reaction time, as it directly affects the desired molecular ratios of the final yield, which is one factor of the end benefit of this present invention. For example, limiting the reaction to 2-4 hours, will give a yield limited to higher molecular size fragments of modified aloe polysaccharides, in contrast, continuing the reaction for a longer period, will cleave the larger polysaccharide units into smaller units, which is the preferred product of this modification process. It is expected to obtain the modified aloe polysaccharide fragments in the following weight percentages.

TABLE 2

Weight percentages of modified polysaccharide fragments

| A | 100-200 kDa | 12-16% w/w |
| B | 1-5 kDa | 25-30% w/w |
| C | <1 kDa | 55-60% w/w |

In the present modification process, the yield is collected after continuing the reaction for 6 hours. To obtain the above molecular weight fractions of modified aloe polysaccharides, the reaction is continued for approximately 6 hours, and the filtered fractions are immediately freeze dried for further use. According to an embodiment of the present invention, the formulation of the active ingredient in combination is as follows: 100-200 kDa, 12-16% w/w (A) 12; 1-5 kDa, 25-30% w/w (B) 14; <1 kDa, 55-60% w/w (C) 16 (see Table 2). The filtered fraction group of <1 kDa, 55-60% w/w (C) 16 further comprises the at least sixteen naturally occurring amino acids, which help the skin to maintain its natural skin pH, at an optimum level.

Figure 1B:
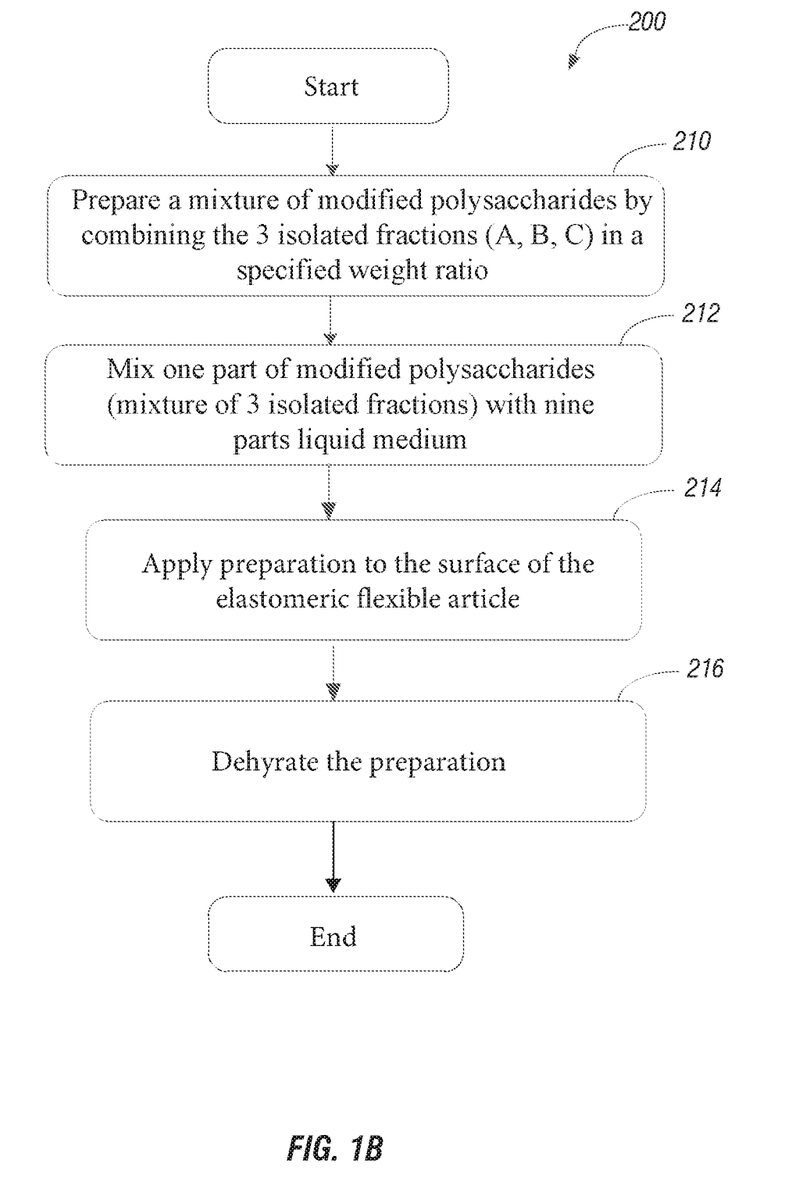
FIG. 1B illustrates a method for making an elastomeric flexible article having a preparation of modified polysaccharides, according to an embodiment of the present invention.

As shown in FIG. 1B, one method 200 of preparing the coating 10 using the isolated aloe fractions at a weight ratio of 10:30:60 of A 12, B 14, and C 16 respectively for application to the inside surface of an article (step 210), is to take one part of the above mixture of isolated aloe fractions and dissolve the mixture in nine parts of a mixing medium, preferably, water (step 212). Mixing is done by using a stirrer at 300-400 rpm, for at least half an hour. An example of the modified aloe coating 10 using the isolated aloe fractions at a weight ratio of 10:30:60 of A 12, B 14, and C 16 respectively is then applied to the inside surface 6 of the polymer elastomeric flexible article, for example, a glove 2 either by spraying or dipping (step 214). The coated gloves 2 are dried at a temperature between 45° C.-55° C. for a duration of 20-30 minutes (step 216).

The mixture of modified aloe polysaccharides is incorporated on the inside surface 6 of the polymer elastomeric flexible article, for example a glove 2, by means of spraying or immersing the object in the coating 10. The coating 10 is attached to the inside surface 6 of the glove 2 through a dehydration process, where the coated gloves 2 are dried in a pre-heated oven at 45° C.-55° C. more preferably at 50° C., and the drying process continues to about 20-30 minutes. The temperature of the hot air is maintained at the above range to avoid the loss of active ingredients in the inside surface 6. Additionally, this process can be accomplished by a hot air oven with a device to spray and tumble simultaneously during drying to distribute the coating 10 uniformly on the glove 2 surface.

FIG. 3 illustrates a cross sectional view of a polymer elastomeric flexible article, such as a glove 2 comprising a coating 10 (dried preparation) on the inside surface 6 of the article, the coating 10 comprises modified aloe polysaccharides in combination with naturally occurring amino acids, according to an embodiment of the present invention. The cross sectional view shows the article having an indeterminate or variable length and thickness as well as a magnified view of the coating thickness for reference purposes. The elastomeric base layer can be a glove, such as a disposable, fluid impermeable examination type glove or disposable protective glove 2. An elastomeric flexible article, according to some embodiments of the present invention is a disposable protective glove 2, but other forms of articles may also be used, such as protective articles worn on, or to cover, a portion of the skin. The disposable glove 2 can be made of resinous materials such as vinyl or the like or polymer materials such as acrylonitrile or other common choices. Three commonly used materials for making gloves 2 are natural rubber latex, acrylonitrile, and polyvinyl chloride, although any other elastomeric materials may also be used. Still other materials, for example, polyurethane, chloroprene, neoprene, butadiene, or the like, or any elastomeric material known to those with ordinary skill in the art may also be used.

The disposable glove 2 includes at least a layer 8 made from a polymer elastomeric base. The layer 8 comprises an inside surface 6 and an outside surface 4, the outside surface 4 faces the external environment and the inside surface 6 faces the user's skin when the glove 2 is worn by the user. The coating 10 can comprise of a mixture of the modified aloe fractions with a preferred formulation of 100-200 kDa-12-16% w/w (A) 12, 1-5 kDa-25-30% w/w (B) 14, and less than 1 kDa-55-60% w/w (C) 16. More preferably, the formulation comprises 100-200 kDa at 12% w/w (A) 12, 1-5 kDa at 28% w/w (B) 14, and less than 1 kDa at 60% w/w (C) 16.

Figure 4:
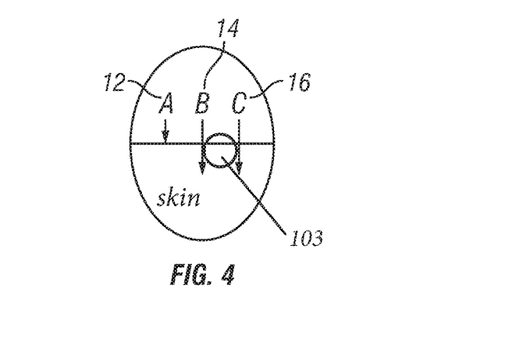
FIG. 4 is a detail view taken from FIG. 3 illustrating the modified aloe polysaccharides penetrating the stratum corneum, according to an embodiment of the present invention.

Once a user wears the glove 2, the coating 10 comes into direct contact with the users' skin and the coating 10 dissolves due to the warm and moist environment created inside. FIG. 4 is a detailed view of FIG. 3 at 101. As illustrated in FIG. 4, the 100-200 kDa, 12-16% w/w (A) 12 remains on the outer surface of the user's skin but the 1-5 kDa, 25-30% w/w (B) 14, and less than 1 kDa, 55-60% w/w (C) 16 size molecules are absorbed into the user's skin, using a passive process through the intracellular routes of the stratum corneum. The modification of aloe polysaccharides into lower molecular sizes increases the effective dermal penetration of the aloe polysaccharide into the skin.

Figure 5:
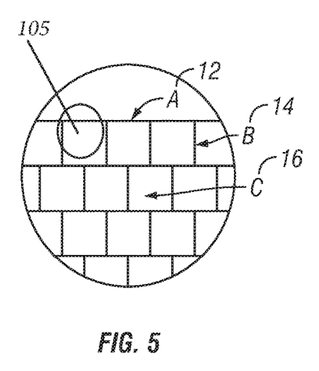
FIG. 5 is a detail view taken from FIG. 4 illustrating various size aloe polysaccharides targeting particular sites at the stratum corneum, according to an embodiment of the present invention.

FIG. 5 illustrates the target sites in the stratum corneum where the specific aloe fractions bind to. FIG. 5 is a detailed view of FIG. 4 at 103. The modified aloe polysaccharides from fraction A 12 bind to the outer surface of the user's skin, fraction B 14 bind to the intercellular lipids and fraction C 16 bind to the corneocytes in the stratum corneum.

Figure 6:
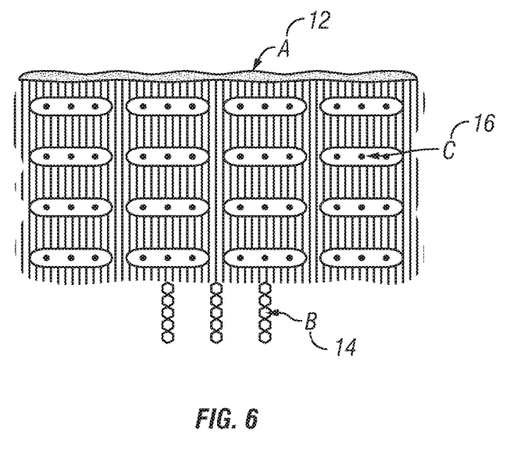
FIG. 6 is a detail view taken from FIG. 5, according to an embodiment of the present invention.

FIG. 6 is a detailed version of FIG. 5 at 105 illustrating that the modified aloe polysaccharides from fraction A 12 (the larger fractions (100-200 kDa, 12-16% w/w) remain on the outer skin surface due to its bulkiness and inability to penetrate through the user's skin. This provides an additional soothing effect to the skin surface by binding water molecules from the surrounding air. The modified aloe polysaccharides from fraction B 14 (1-5 kDa, 25-30% w/w) bind to the intercellular lipids and the modified aloe vera polysaccharides from fraction C (<1 kDa, 55-60% w/w) 16 bind to the corneocytes in the stratum corneum. Fraction B 14 (1-5 kDa, 25-30% w/w) is unlikely to penetrate through intracellular routes due to its molecular size.

Figure 7:
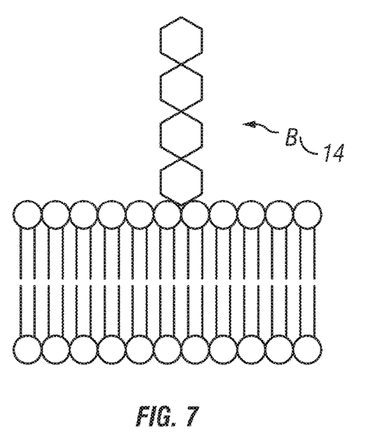
FIG. 7 illustrates binding of 1-5 kDa, 25-30% w/w modified aloe polysaccharide to the inter-cellular lipids in the stratum corneum, according to an embodiment of the present invention.
Figure 8:
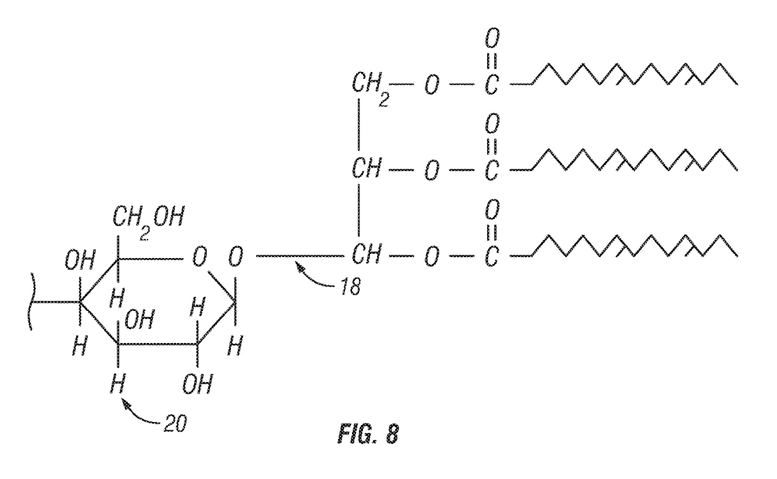
FIG. 8 illustrates formation of a glycosidic bond with a hydroxyl group of the 1-5 kDa, 25-30% w/w and hydrophilic head of the lipid, according to an embodiment of the present invention.

FIG. 7 illustrates binding of fraction B 14 (1-5 kDa, 25-30% w/w) modified aloe polysaccharide to the intercellular lipids in the stratum corneum, according to an embodiment of the present invention. This binding is done by forming a glycosidic bond 18 with a hydroxyl group of the modified medium aloe polysaccharide sugar and hydrophilic head of the lipid, as illustrated in FIG. 8. These medium polysaccharide fractions 14 (also called glycolipids when bound with lipids) create a shielding environment in the lipid bi-layer, facilitating to reduce the trans-epidermal water loss, by trapping the evaporating moisture from deeper skin layers. Furthermore, glycolipids are known to act as precursors namely, 'glucosylceramide' in ceramide formation. Ceramide have been found to be a major lipid in the stratum corneum, which contributes to skin barrier function.

As illustrated in FIGS. 4-7, modified aloe polysaccharide fractions B 14 (1-5 kDa, 25-30% w/w), can bind with intercellular lipids. These medium sized polysaccharide units are encapsulated in liposomes to facilitate penetration through intercellular lipid spaces. These liposomes are dissolved in the intercellular lipid and resealed the medium sized polysaccharide.

The smaller aloe fractions C 16 (less than 1 kDa, 55-60% w/w) can penetrate through the intracellular routes in the corneocytes, of the stratum corneum as natural moisturizing factors. A combination of these modified aloe polysaccharide molecules in different sites synergistically increases the water binding capacity of the stratum corneum.

Figure 9:
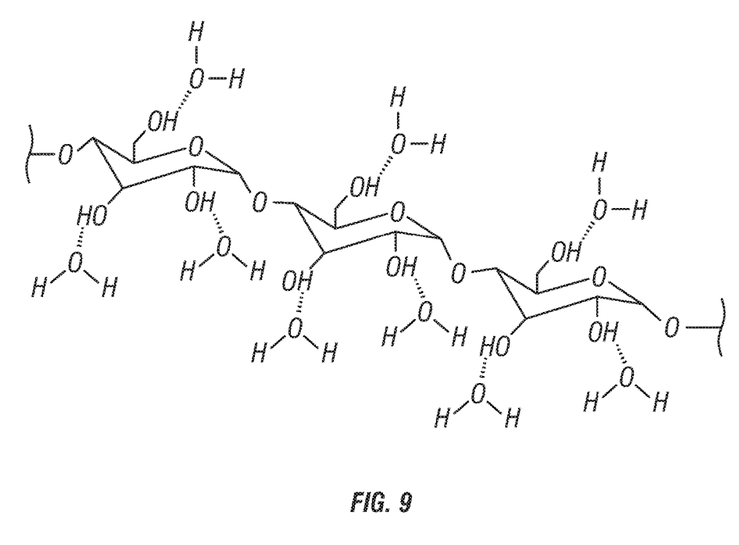
FIG. 9 illustrates a mechanism of water binding with a modified aloe polysaccharide fraction, according to an embodiment of the present invention.

FIG. 9 illustrates a mechanism of water binding with a modified aloe polysaccharide fraction, according to an embodiment of the present invention. This mechanism effectively increases skin moisture by increasing the water holding capacity of the stratum corneum via delivering aloe polysaccharide fractions bound to water molecules. This is needed because the skin's moisture retention ability is compromised from frequent handwashing and the present invention improves it. The modified aloe polysaccharide fractions from A (100-200 kDa, 12-16% w/w) 12, provide additional soothing effect to the skin through absorbing moisture from the surrounding air by remaining on the skin's outer surface. The water binds with aloe polysaccharide fractions as illustrated in FIG. 9.

As a summary, these modified aloe polysaccharide fractions can bind to three different locations as illustrated in FIG. 6 in the stratum corneum, thus increasing water retention capacity in the skin, and eventually increasing the skin's hydration. Furthermore, the mechanism of water binding with the above-mentioned aloe fractions is illustrated in FIG. 9. The water molecules form hydrogen bonds with the hydroxyl group of the aloe polysaccharide fractions.

While particular embodiments of the present invention have been shown and described, it will be obvious to those of skills in the art that based upon the teachings herein, changes and modifications may be made without departing from this exemplary embodiment(s) of the present invention and its broader aspects. Therefore, the appended claims are intended to encompass within their scope all such changes and modifications as are within the true spirit and scope of this exemplary embodiment(s) of the present invention.

What is claimed is:

1. A skin hydrating elastomeric article comprising:
    a skin contacting inner surface and;
    a dry coating of three fractions of modified polysaccharides, the coating being dissolvable to release the three fractions of modified polysaccharides, each fraction targeting a different site in the stratum corneum,
    wherein the three fractions are obtained by a method comprising: mixing one part of a polysaccharide content having a molecular weight from 50-200 kDa with nine parts of a liquid medium; filtering a first fraction of a first range of molecular sized polysaccharides from the mixture; reacting the mixture with an enzyme for a period of time and generating a reacted product; filtering a second fraction of a second range of molecular sized polysaccharides from the reacted product; filtering a third fraction of a third range of molecular sized polysaccharides from the reacted product.

2. The elastomeric article according to claim 1, wherein the elastomeric material is selected from a group consisting of vinyl, acrylonitrile, natural rubber latex, polyvinyl chloride, polyurethane, chloroprene, neoprene, and butadiene.

3. The elastomeric article according to claim 1, wherein the modified polysaccharides are sourced from aloe.

4. The elastomeric article according to claim 1, wherein the modified polysaccharides comprise a molecular weight less than 1 kDa to 200 kDa.

5. The elastomeric article according to claim 4, wherein a first fraction of modified polysaccharides has a molecular weight from 100-200 kDa contains from 12 to 16% by weight of modified polysaccharides.

6. The elastomeric article according to claim 4, wherein a second fraction of modified polysaccharides has a molecular weight from 1-5 kDa contains from 25 to 30% by weight of modified polysaccharides.

7. The elastomeric article according to claim 4, wherein a third fraction of modified polysaccharides has a molecular weight of less than 1 kDa contains from 55 to 60% by weight of the modified polysaccharides.

8. The elastomeric article according to claim 7, wherein the third fraction of modified polysaccharides comprise sixteen naturally occurring amino acids.

9. The elastomeric article according to claim 1, wherein the three fractions of modified polysaccharides have a preferred formulation of 100-200 kDa-12% w/w, 1-5 kDa-28% w/w and less than 1 kDa-60% w/w.

10. A process of making a preparation of modified polysaccharides, the method comprising:
    mixing one part of a polysaccharide content having a molecular weight from 50-200 kDa with nine parts of a liquid medium;
    filtering a first fraction of a first range of molecular sized polysaccharides from the mixture;
    reacting the mixture with a β-D-mannanase for a period of time and generating a reacted product;
    filtering a second fraction of a second range of molecular sized polysaccharides from the reacted product;
    filtering a third fraction of a third range of molecular sized polysaccharides from the reacted product.

11. The process according to claim 10, wherein the first fraction is filtered from a membrane having a molecular size cut-off of 100 kDa and the first range of molecular sized polysaccharides is about 100 kDa to about 200 kDa.

12. The process according to claim 10, further comprising freeze drying the first fraction.

13. The process according to claim 10, wherein the β-D-mannanase has a concentration of approximately 2 grams per 100 grams of the polysaccharide content.

14. The process according to claim 10, wherein the second fraction is filtered through a membrane having a molecular size cut-off of 5 kDa and the second range of molecular sized polysaccharides is about 1 kDa to about 5 kDa.

15. The process according to claim 10, further comprising freeze drying the second fraction.

16. The process according to claim 10, wherein the third fraction is filtered through a membrane having a molecular size cut-off of 1 kDa.

17. The process according to claim 10, further comprising freeze drying the third fraction and the third range of molecular sized polysaccharides is less than 1 kDa.

18. The process according to claim 10, wherein a reaction temperature of the reacting step is from about 50 degrees to about 60 degrees centigrade.

19. The process according to claim 10, wherein a duration of the reacting step is about six hours.

20. The process according to claim 10, further comprising:
   freeze drying the first fraction after filtering the first fraction, freeze drying the second fraction after filtering the second fraction, freeze drying the third fraction after filtering the third fraction; and
   combining a freeze dried first fraction, freeze dried second fraction and freeze dried third fraction at a weight ratio of about 10:30:60.

21. The process according to claim 10, further comprising the steps of:
   freeze drying the first fraction after filtering the first fraction;
   encapsulating the filtered second fraction with liposomes;
   freeze drying the encapsulated second fraction;
   freeze drying the third fraction after filtering the third fraction;
   combining the freeze dried first fraction, freeze dried encapsulated second fraction and freeze dried third fraction at a weight ratio of about 10:30:60;
   applying the preparation of modified polysaccharides comprising a mixture of an effective amount of the freeze dried first fraction, the freeze dried second fraction, the freeze dried third fraction and a liquid medium, to a skin-contacting inner surface of the elastomeric flexible article; and
   dehydrating the preparation.

22. A method of making an elastomeric flexible article having a preparation of modified polysaccharides made according to the process of claim 10, the method comprising:
   applying the preparation of modified polysaccharides comprising a mixture of an effective amount of the filtered first fraction, the filtered second fraction, the filtered third fraction and a liquid medium, to a skin-contacting inner surface of the elastomeric flexible article; and
   dehydrating the preparation.

23. An elastomeric flexible article comprising:
   a layer of fluid impermeable elastomeric material comprising an inside surface having a dried preparation of modified polysaccharides and amino acids, the dried preparation being closest to skin when the article is in use;
   the modified polysaccharides comprising a first fraction of modified polysaccharides from 100-200 kDa at 12 to 16% w/w, a second fraction of modified polysaccharides from 1-5 kDa at 25 to 30% w/w, and a third fraction of modified polysaccharides from less than 1 kDa at 55 to 60% w/w;
   each fraction of modified polysaccharides and amino acids is activated by a warm and moist environment on the skin,
   wherein the three fractions are obtained by a method comprising: mixing one art of a polysaccharide content having a molecular weight from 50-200 kDa with nine parts of a liquid medium; filtering, a first fraction of a first range of molecular sized polysaccharides from the mixture; reacting the mixture with an enzyme for a period of time and generating a reacted product; filtering a second fraction of a second range of molecular sized polysaccharides from the reacted product; filtering a third fraction of a third range of molecular sized polysaccharides from the reacted product.

\* \* \* \* \*